United States Patent [19]

Wilson et al.

[11] Patent Number: 5,698,326

[45] Date of Patent: Dec. 16, 1997

[54] PERACID COMPOUNDS

[75] Inventors: Sharon Lesley Wilson, Warrington; Johnathan McAdam, St. Helens; John Phillip Sankey, Warrington, all of United Kingdom

[73] Assignee: Solvay Interox Limited, Warrington, England

[21] Appl. No.: 406,880

[22] PCT Filed: Sep. 20, 1993

[86] PCT No.: PCT/GB93/01975

§ 371 Date: Apr. 21, 1995

§ 102(e) Date: Apr. 21, 1995

[87] PCT Pub. No.: WO94/07855

PCT Pub. Date: Apr. 14, 1994

[30] Foreign Application Priority Data

Sep. 25, 1992 [GB] United Kingdom ............... 9220347

[51] Int. Cl.$^6$ .................. C07C 409/40; C07C 407/00
[52] U.S. Cl. ................... 428/403; 427/215; 427/218; 427/219; 427/220; 428/404; 428/405; 428/446; 428/447

[58] Field of Search ............... 428/446, 447, 428/403, 404, 405; 427/215, 218, 219, 220

[56] References Cited

PUBLICATIONS

Greig et al. "Preparation of Polymer Resin and Inorganic Oxide Supported Peroxy–acids and their use in the Oxidation of tetrahydrothiophene" European Polymer Journal, vol. 16, pp. 293–298 (1980).

Primary Examiner—D. S. Nakarani
Attorney, Agent, or Firm—Larson & Taylor

[57] ABSTRACT

Organic peracids supported on inorganic macromolecular supports and a process for preparing them are provided. The peracids have general chemical formulae: Q—O—Si—A—NR—X—CO$_3$H (I) wherein Q represents the inorganic support, A is an alkylene or arylene group, R represents hydrogen, alkyl or an aryl group and X represents an optionally substituted alkylene or arylene group, or Q—O—Si—A—N X'—CO$_3$H (II) where Q and A are as defined above, and X' represents an optionally substituted alkylene or arylene group. The peracids have improved stability and recovery characteristics compared with those of the prior art.

32 Claims, No Drawings

PERACID COMPOUNDS

BACKGROUND OF THE INVENTION

This invention concerns organic peracids, and more specifically, organic peracids bonded to an inorganic support.

Organic peracids have found many applications throughout industry because of their oxidative nature. For example, they are widely employed as oxidants in organic reactions, including use in epoxidation reactions, where certain examples have been found to be useful selective oxidants. Examples are also used to disinfect and reduce the chemical oxygen demand of aqueous effluent streams.

In the majority of applications for peracids, in order for the peracid to have an effect on the desired substrate it has often been found necessary for the peracid to be employed as either a solution, or in some other form, for example a powder, which is capable of producing an in-situ solution of the peracid. Once the peracid has acted on the substrate, it is often reduced to form the corresponding acid, which has no further oxidative activity. Such spent reagent can then either be discarded or can be recovered from the oxidation medium for possible recycling or use in other processes. When the peracid is a cheap and readily produced one such as peracetic acid, it is often acceptable for the peracid to be discarded, unless there are special circumstances necessitating or permitting its easy recovery. However, in many cases, it is desirable that discarding the spent reagent is avoided, if possible, because it represents a waste of chemical raw materials and also adds to process and effluent treatment costs. This is particularly so in cases where the peracid employed is more complex and/or more expensive to produce than simple peracids such as peracetic acid.

One option for reducing the wastage of chemicals is to regenerate the peracid from the acid in the oxidation medium by adding an oxidising agent. Unfortunately, this approach suffers from the drawback that the concentration of acid remaining in the oxidation medium is often relatively low. This means that the reaction kinetics and/or equilibrium for the production of the peracid are unfavourable for a rapid and economic reaction to occur.

Another option for reducing chemical wastage is to separate the remaining acid from the reaction medium for conversion back to peracid, or for use in other processes. There are many disadvantages to this where conventional peracids are employed. For example, if both the oxidation product and the spent reagent are solids, purification stages are necessary. If the spent reagent remains in solution in the oxidation medium, it may be necessary, for example, to evaporate off the solvent until the spent reagent precipitates, but even this does not guarantee the purity of the acid produced and further purification can be necessary. In many cases, such separations require specialised plant, which adds to the cost of the process, as well as increasing the need for space.

Nevertheless, it remains desirable that the spent reagent should be recoverable from the oxidation medium, preferably by the use of a relatively simple separation process such as filtration. One option to achieve this is to employ the peracid in a form such that the recovery of the acid could easily be achieved. One possibility that has been explored is to physically absorb a peracid on an insoluble support, but this approach has the problem that the peracid is attached to the support by relatively weak intermolecular forces only, so that it is relatively easy for the peracid or corresponding acid to dissolve and therefore to be lost from the support.

An alternative approach was suggested by Sherrington et al in European Polymer Journal Vol 16, pp293–8. Sherrington's process comprised chemically bonding an aromatic organosilane containing a benzyl chloride moiety to an inorganic macromolecular support containing pendant hydroxy groups, or modifying an inorganic-supported organic group to include a benzyl chloride moiety. The benzyl chloride moiety was then converted to a benzaldehyde moiety, which was then oxidised to produce a peracid. The supported peracids produced by Sherrington's process were found in the studies leading to the present invention to have poor chemical stability and so could not conveniently be stored at ambient temperatures. The trials also showed that peracids had a physical form which rendered their recovery from the preparative reaction medium by filtration difficult, and would also make it difficult to recover and recycle the peracid or corresponding acid when employed as an oxidant.

It is an object of one aspect of the present invention to provide organic peracids chemically bonded to an inorganic support which have improved storage stability and/or superior product recovery characteristics compared with those produced by Sherrington.

It is a second objective of another aspect of the present invention to provide a process for producing organic peracids chemically bonded to an inorganic support which have improved storage stability and/or superior product recovery characteristics compared with those produced by Sherrington.

It is a third objective of certain embodiments of the present invention to provide a process for preparing organic peracids chemically bonded to an inorganic support that employs fewer preparation stages compared with the process demonstrated by Sherrington.

It is a fourth objective of certain embodiments of the present invention to provide amido or imido peracids chemically bonded to an inorganic support.

SUMMARY OF THE INVENTION

According to the present invention, there are provided organic peracids chemically bonded to an inorganic support, characterised in that they contain a group either of general chemical formula:

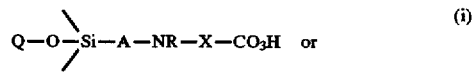 (i)

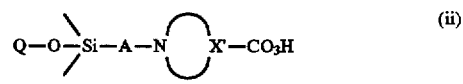 (ii)

where Q represents the inorganic support, A is an aliphatic and/or aromatic bridging group, R represents hydrogen, an alkyl or an aryl group, or a group having the formula X—CO$_3$H, X represents an optionally substituted alkylene or arylene group and X' represents an optionally substituted alkylene or arylene group.

According to a second aspect of the present invention, there is provided a process for producing organic peracids chemically bonded to an inorganic support, characterised in that they contain a group either of general chemical formula:

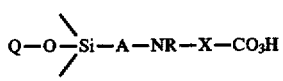 (i)

or

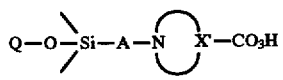 (ii)

where Q represents the inorganic support, A is an aliphatic and/or aromatic bridging group, R represents hydrogen, an alkyl or an aryl group, or a group having the formula X—CO₃H, X represents an optionally substituted alkylene or arylene group and X' represents an optionally substituted alkylene or arylene group comprising the following stages:

Stage (i) Reacting an inorganic support having at least one pendant hydroxy group of formula Q—OH with a silane having the general chemical formula R'₃Si—A—NHY, where A is as defined above, R' represents an alkoxy group and Y represents hydrogen, alkyl or aryl groups, or a group having the formula X-CO₃H to form an intermediate of formula

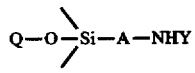

Stage (ii) Reacting the intermediate from Stage (i) with a compound of formula Z—X—D or ZZ'—X'—D where X and X' are as defined above, Z and Z' represent an oxy- or halogen-containing leaving group and D represents a carboxylic acid group or a functionality capable of conversion thereto to form an intermediate of formula

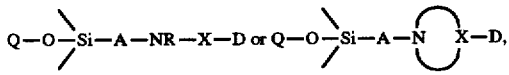

and

Stage (iii) Reacting the intermediate from Stage (ii) with hydrogen peroxide in the presence of a strong acid thereby producing an inorganic-supported peracid having one of the general formulae described above.

DESCRIPTION OF PREFERRED EMBODIMENTS

The aliphatic and/or aromatic bridging group A in inorganic-supported peracids according to the present invention can comprise linear or branched alkylene groups. It can also comprise one or more aromatic rings which may be substituted by one or more alkyl or aryl groups. In many preferred embodiments, the bridging group comprises a linear alkylene chain having from 1 to 10 carbon atoms, preferably from 2 to 5 carbon atoms. The bridging group can also comprise one or more O or N atoms in place of one or more carbon atoms.

When the inorganic-supported peracids according to the present invention have the general chemical formula

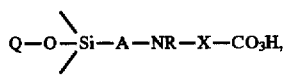

the group X can be an optionally substituted alkylene or arylene group, which can include a carbonyl group at the alpha position relative to the N. In certain embodiments, X comprises a linear alkylene chain having up to about 18 carbon atoms, preferably from about 10 to about 14 carbon atoms. In other embodiments, X comprises at least one aromatic ring which may be directly bonded to either or both of N and CO₃H, or may be separated from either or both of them by an alkylene group. In many preferred embodiments, the aromatic ring is bonded directly to the CO₃H. The group R can be hydrogen or an alkyl or aryl group or a group having the formula X—CO₃H. When R has the formula X—CO₃H, the group can either be the same or have a different structure to the other X—CO₃H in the peracid.

When the inorganic-supported laeracids according to the present invention have the general chemical formula

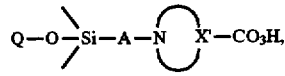

the group X' can be an optionally substituted alkylene or arylene group. It will be recognised that the bond between N and X' can comprise a C=N double bond, but in many embodiments, the bonds between N and X' are such that they form a cyclic amino or imido group, preferably having from 5 to 7 atoms in the ring. In certain embodiments, the N is bonded to two carbonyl groups which comprise part of X'. Preferably, the two carbonyl groups are bonded to an aromatic ring. Most preferably, the aromatic ring is a benzene ring, and the carbonyl groups are bonded to adjacent carbons in that ring.

X or X' often comprises up to about 22 carbon atoms, preferably between 4 and 16 carbon atoms and most preferably from about 6 to about 10 carbon atoms.

The peracid group CO₃H can be a substituent of any carbon within the molecule X or X'. In many embodiments, the peracid group is separated from N by at least 2 carbon atoms, preferably from about 3 to about 6 carbon atoms. In some embodiments, N is bonded to two carbonyl groups which are themselves bonded to adjacent carbons in a benzene ring, the peracid group is most preferably bonded directly to the benzene ring in the meta position relative to one carbonyl group and in the para position relative to the other carbonyl. In other embodiments the peracid group is spaced from the benzene ring by an aliphatic group, such as an alkylene group containing from 1 to 6 linear carbons, optionally substituted with an alkyl or aryl substituent. This gives a separation between N and the peracid group in such embodiments of at least 4 carbons.

The inorganic support, Q, employed in the present invention can be any inorganic macromolecule which contains at least one pendant hydroxy group as such or can be chemically modified to introduce such groups. In many embodiments, the inorganic support comprises one or both of aluminium and silicon based compounds. Silicon-based inorganic supports which can be employed to produce the compounds according to the present invention include silica gel and diatomaceous earth. Suitable aluminium based inorganic supports include alumina. Examples of suitable inorganic supports including both aluminium and silicon are aluminosilicates, particularly naturally occurring clays such as bentonites, for example, montmorillonite, and synthetic clays such as synthetic hectometers, for example that available from Laporte Industries Limited under the Trademark "Laponite". It will also be recognised that it is possible to employ mixtures of different inorganic supports.

The inorganic supports are typically employed as a free-flowing powder. The surface area of the inorganic support is often in the range of from about 50 m²/g to about 1000 m²/g, preferably from about 200 m²/g to about 800 m²/g.

In a particularly preferred embodiment of the present invention, the inorganic support is silica gel having a surface area in the range of 250 to 350 m²/g, A is a linear $(CH_2)_3$ group and N is bonded to two carbonyl groups fused with a benzene ring to form a phthalimido group, the peracid group being bonded directly to the benzene ring in the meta position relative to one carbonyl group and in the para position relative to the other carbonyl. This gives an inorganic-supported peracid having the formula:

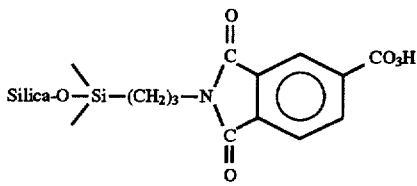

In the process according to the present invention, it is possible to employ an inorganic support that contains at least one pendant hydroxy group without any pre-treatment, but in many cases, it is preferable that the support is pre-treated in order to increase the numbers of pendant hydroxy groups and so increase the number of sites for attaching organic substituents. One convenient pre-treatment is to reflux the inorganic support in a solution of an inorganic acid for about 2 to 6 hours. Both dilute or concentrated solutions can be employed. One particularly suitable inorganic acid is hydrochloric acid. After such an acid treatment, the inorganic support is preferably washed free of acid with water, typically until the pH of the washings reaches 7.

Following any pre-treatment, the inorganic support is often dried. This can be achieved by storing the support under a vacuum of, for example less than about 50 mmHg, preferably less than about 10 mmHg, at elevated temperature. A typical storage time would be 2 days at a temperature of 130° C., although it is possible to envisage faster drying methods involving, for example, higher temperatures.

Stage (i) of the process according to the present invention comprises reacting the dried inorganic support with a trialkoxysilane. The trialkoxysilane is conveniently chosen according to the desired supported peracid it is desired to produce. In many cases it is preferable that the alkoxy groups are low molecular weight alkoxy groups. A particularly suitable silane has been found to be aminopropyltrimethoxysilane, $(MeO)_3Si(CH_2)_3NH_2$, where $A=(CH_2)_3$. This reaction can suitably be achieved by dissolving the silane in a suitable organic solvent containing a small amount, often up to about 25%, preferably up to about 15%, of the volume of silane employed, of water, and refluxing in the presence of the inorganic support until substantially all of the pendant hydroxy groups has reacted with the silane. Suitable organic solvents include toluene, hydrocarbons such as petroleum ethers, halocarbons such as chlorobenzene and ethers, but is preferably toluene. Typical reaction times do not exceed 24 hours, and in many cases are selected in the range of 3 to 10 hours. The intermediate from stage (i) can be obtained by suitable separation means, for example, filtration or centrifugation, and preferably is then washed with a volatile organic solvent to remove substantially all of any remaining reaction liquor. Suitable volatile organic solvents comprise methanol, ethanol, propanol or acetone. The washed product can then be dried thoroughly. Preferably, the drying is accomplished under vacuum of, for example less than about 50 mmHg, preferably less than about 10 mmHg, at elevated temperatures up to about 90° C. for periods up to about 72 hours.

Stage (ii) of the process according to the present invention comprises reacting the intermediate from stage (i) with a suitable compound containing one or two oxy- or halogen-containing leaving groups, Z and Z', and a carboxylic acid group or group capable of conversion thereto, D. It will be recognised that the choice of such a group will often most conveniently be such that the acid produced in stage (ii) can be peroxidised in stage (iii) to form the desired inorganic supported peracid, but that this need not necessarily be the case because it is possible to modify the product of stage (ii) in further stages to produce the particular compound desired. This will be particularly convenient if it is not possible to identify a compound that will react with an N—H group to produce the desired molecule in a single stage. Suitable oxy- or halogen-containing leaving groups include

groups, particularly —COCl groups, and also anhydride groups. Particularly suitable anhydrides are those of organic diacids where the acid groups are positioned such that the anhydride produced forms a cyclic group, for example maleic anhydride or phthalic anhydride. The most suitable anhydride has been found to be trimellitic anhydride. Typical groups that are capable of conversion to a carboxylic acid comprise —$CH_3$ groups, —CHO groups and ester groups.

The reaction between the intermediate produced in stage (i) and the compound of formula Z—X—D or ZZ'—X'—D conveniently takes place in a suitable solvent, often under reflux conditions. Particularly suitable solvents are short chain aliphatic acids, particularly acetic acid. The reaction is preferably continued until substantially all of the intermediate from stage (i) has reacted with the compound of formula Z—X—D or ZZ'—X'—D. Typical reaction times are unlikely to be longer than about 24 hours and are preferably from about 2 to 10 hours. The intermediate from stage (ii) can be obtained by a suitable separation process such as filtration or centrifugation, and preferably the product washed with a volatile organic solvent to remove substantially all of any remaining reaction liquor. Suitable volatile organic solvents comprise methanol, ethanol, propanol or acetone. The washed product is preferably then dried thoroughly. Preferably, the drying is accomplished under vacuum of, for example less than about 50 mmHg, preferably less than about 10 mmHg, at elevated temperatures up to about 90° C. for periods up to about 72 hours.

It will be recognised that in both stage (i) and (ii), it is possible to employ the reagents in a wide range of mole ratios including stoichiometric mole ratios. However, it will also be recognised that in order to obtain optimum loadings on the inorganic support it can be advantageous to use a molar excess over the stoichiometric amount of the silane or compound of formula Z—X—D or ZZ'—X'—D. Any remaining unreacted reagent can usually be removed by washing the inorganic support with a suitable solvent, thus avoiding excessive contamination of the support.

Hereinbefore there has been described a two stage process for producing a compound containing a carboxylic acid, or group capable of conversion thereto, bonded to an inorganic support via a silane in which the first stage comprises bonding the silane to the inorganic support and the second stage comprises bonding the compound containing a carboxylic acid, or group capable of conversion thereto, to the silane. In other embodiments, the reaction sequence can be reversed, whereby in the first stage, the alkoxysilane of formula R'$_3$Si—A—NHY is reacted with the compound of formula Z—X—D or ZZ'—X'—D, and the resultant compound of formula R'$_3$Si—A—NR—X—D or

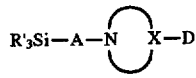

is bonded to the inorganic support in the second stage. In the first stage of the reverse sequence, the reaction is carried out in a suitable solvent for the compound of formula Z—X—D or ZZ'—X'—D but which does not adversely effect the alkoxysilane. Examples of suitable solvents include non-carboxylic acid solvents, such as dimethylformamide, and alcohols. When an alcohol is employed as solvent, it preferably corresponds to the alkoxy groups of the silane. Apart from the nature of the solvent in the first stage, substantially the same conditions can be employed for respectively the silane—support and the compound of formula Z—X—D or ZZ'—X'—D—silane reactions in the reverse sequence as for stages (i) and (ii) above. This produces the same compound as when the trialkoxysilane is first reacted with the inorganic support, and which can then be peroxidised in stage (iii). These embodiments offer the possibility of producing the supported peracids in substantially a one pot process.

Stage (iii) of the process according to the present invention comprises peroxidising the intermediate produced in stage (ii). The peroxidation process employed can be substantially any process for the oxidation of an organic acid to a peracid. In most cases the peroxidation comprises reacting the acid with hydrogen peroxide in the presence of a strong acid at a temperature not usually greater than about 40° C. The hydrogen peroxide is often employed as a concentrated aqueous solution, typically comprising from about 65 to about 95%, preferably from about 70 to about 90%, by weight, and comprises about 10 to about 30 volume percent of the total stage (iii) reaction mixture. Preferred strong acids comprise sulphuric acid, methanesulphonic acid and phosphoric acid and mixtures thereof. Another possibility is to employ a pre-formed mixture of hydrogen peroxide and sulphuric acid in which an effective amount of Caro's acid is present. It is most convenient that the reaction proceeds at ambient temperature, ie about 20°–25° C. The reaction typically proceeds until substantially all of the supported organic acid has been peroxidised to produce a peracid, or until analysis of the reaction mixture indicates that none of the oxidant remains. At this point, further oxidant may be added, or the reaction may be terminated. Typically, the mole ratio of oxidant to supported acid employed in stage (iii) is at least stoichiometric, and can be up to up to 200:1, because it is possible that if only a stoichiometric ratio is employed, any oxidant decomposition that may occur will result in incomplete peroxidation of the desired peracid. Typically, the strong acid is employed at a concentration of about 40 to 90, preferably about 65 to 85, volume percent of the total stage (iii) reaction mixture. In one particular embodiment, the intermediate from stage (ii) is peroxidised by passing a solution of strong acid and hydrogen peroxide down a column containing the intermediate. The product of stage (iii) can be obtained after quenching the reaction in an ice/water mixture by a suitable separation process, eg filtration or centrifugation, and is conveniently vacuum or air dried at room temperature (20°–25° C.) until no further weight loss occurs, indicating that drying is substantially complete.

The process according to the present invention can be operated as either a batch or continuous process.

The inorganic-supported peracids according to the present invention are suitable for application as oxidants in a wide range of areas, although it will be recognised that the area of application will depend on, for example, the nature of the peracid on the inorganic support. In many cases, the inorganic supported peracids according to the present invention are suitable for similar applications to non-supported peracids. For example, they are suitable for application as disinfectants, bleaching agents, waste water treatment agents and as oxidants in synthetic reactions, including use as epoxidising agents. The excellent stability of the peracids according to the present invention at ambient temperatures means that they can be stored conveniently, and it is not necessary to prepare the peracids immediately prior to use if no suitable refrigerated storage is available.

Because of the bonding to the inorganic support, it is most likely that in the majority of applications, the peracids will function as heterogeneous oxidants. This means that when the oxidation is completed, or the oxidative capacity of the peracids is exhausted, it is very easy to separate the peracid or acid from the oxidising medium by a simple separation technique such as filtration. After suitable washing and drying, if desired, the peracid can then either be employed in another oxidising application if it retains any oxidative capacity, or, if the peracid has been reduced to the corresponding acid, it can be oxidised by a process according to stage (iii) of the present invention to re-generate the peracid. This is a very important feature of the peracids according to the present invention because it allows the efficient recycling of potentially expensive chemicals. In one particular embodiment, the peracid is re-generated by passing a solution of strong acid and hydrogen peroxide down a column containing the inorganic supported acid.

Having described the invention in general terms, specific embodiments will now be described by way of example only.

EXAMPLE 1. PREPARATION OF PROPYLIMIDOPERMELLITIC ACID SUPPORTED ON SILICA GEL.

Pre-Treatment 100 g of silica gel having a surface area of 300 m$^2$/g was refluxed in 350 ml of 2N hydrochloric acid for 4 hours, then cooled, filtered off, washed with demineralised water (DMW) until the pH of the washings was pH 7, washed with acetone and then dried at 130° C.

Stage (i)

50 g of the dried silica gel from the pre-treatment was added to 700 ml of toluene and 25 ml DMW. This mixture was then azeotroped to remove water until no more water was being removed and cooled to room temperature. 5 ml DMW was added and the mixture stirred at room temperature for 30 minutes. 50 mls aminopropyltrimethoxysilane was added, the mixture refluxed for 3 hours, cooled and the functionalised silica filtered off, washed with 50 ml toluene then by soxhlet extraction with 800 ml methanol for 21 hours and then dried at 80° C. under a vacuum of <6 mmHg.

Stage (ii)

30 g of the functionalised silica from stage (i) above, 30 g trimellitic anhydride and 300 g acetic acid were refluxed for 6 hours, and allowed to stand for 18 hours during which time cooling to room temperature occurred. The silica-supported acid was filtered off, washed by soxhlet extraction with methanol for 21 hours and dried at 80° C. under a vacuum of <6 mmHg.

Stage (iii)

10 g of the silica-supported acid from stage (ii) above and 8 ml methanesulphonic acid were stirred at room temperature. 2 ml of an 85% w/w aqueous solution of hydrogen peroxide was added over 1.5 hours, the reaction mixture was allowed to stand for 17 hours, and then quenched with ice. The silica-supported peracid was obtained by vacuum filtration for about 15 minutes as a white granular solid, washed with ice/water until the pH of the washings reached pH3 to 5, and vacuum dried over $P_2O_5$.

Analysis of the product of stage (iii) above showed the product to contain an Available oxygen (avox) content of 0.8% by weight. After 12 weeks storage at 32° C., 42% of the initial avox remained.

EXAMPLE 2—USE OF VACUUM DRYING OF SUPPORTED PERACID

The procedure of Example 1 above was followed, except that air drying was employed at each stage to give a product having an initial Avox of 0.52% by weight with 30% of the initial avox remaining after 12 weeks storage at 32° C.

EXAMPLE 3—USE OF MONTMORILLONITE AS INORGANIC SUPPORT

The procedure of Example 1 above was followed, except employing montmorillonite having a surface area of 220–270 $m^2/g$ as the inorganic support. This gave a supported peracid having an initial avox of 0.33% by weight with 42% of the initial avox remaining after 8 weeks storage at 32° C.

EXAMPLE 4—USE OF CONCENTRATED ACID IN PRE-TREATMENT

The procedure of Example 1 above was followed except that the pre-treatment employed 350 ml of 36% w/w hydrochloric acid solution. This gave a supported peracid having an initial avox of 0.5% by weight.

EXAMPLE 5—NO AZEOTROPE EMPLOYED

The procedure of Example 1 above was followed, except that in stage (i), 50 g of silica was dispersed in 200 ml toluene with no addition of 25 ml DMW or azeotroping, and only 10 ml of aminopropyltrimethoxysilane was employed. This gave a supported peracid having an initial avox of 0.33% by weight.

EXAMPLE 6—USE OF SILICA GEL HAVING A SURFACE AREA OF 675 $m^2/g$

The procedure of Example 1 above was followed, except that silica gel with a surface area of 675 $m^2/g$ was employed. This gave a supported peracid having an initial avox of 0.32% by weight.

EXAMPLE 7—USE OF SILICA GEL HAVING A SURFACE AREA OF 480 $m^2/g$

The procedure of Example 1 above was followed, except that silica gel with a surface area of 480 $m^2/g$ was employed.

This gave a supported peracid having an initial avox of 0.67% by weight with 46% of the initial avox remaining after 8 weeks storage at 32° C.

COMPARISON PREPARATION OF PRIOR ART INORGANIC SUPPORTED PERACID

The method described by Sherrington et al in European Polymer Journal Vol 16, p294 was followed, except that for reasons of chemical availability, the silane employed was $Cl_3SiCH_2CH_2$—Ph—$CH_2Cl$ to produce the product 4b in column 2 directly. On completion of the process according to Sherrington et al, the supported peracid was obtained by vacuum filtration. The filtration took greater than 2 hours to complete, and gave a yellow product having an avox of 0.29% by weight. Only 27% of the initial avox remained after 4 weeks storage at 32° C.

The results of Examples 1 to 7 show that the inorganic-supported peracids, according to the present invention have superior stability compared with those according to the prior art, and that the process according to the present invention produces inorganic supported peracids having superior handling characteristics compared with the prior art process.

EXAMPLE 8. USE OF INORGANIC SUPPORTED PERACID IN EPOXIDATION 1 g of cyclohexene, 40 $cm^3$ of dichloromethane and 3.07 g of the product of Example 1 above were stirred in a glass reactor fitted with a condenser for 3 hours at 25° C. The solution was then washed with 10% sodium sulphite solution until no peroxide remained as evidenced by a negative starch test, and then washed with 5% sodium bicarbonate solution. The inorganic-supported acid remaining was recovered by filtration. The dichloromethane layer was then separated and analysed by Gas Chromatography. The analysis showed that substantially no cyclohexene remained, and that the only product was cyclohexene epoxide.

This result demonstrates that supported peracids according to the present invention can be used as oxidants in chemical synthesis, and that it is very easy to recover the supported peracid or acid on completion of the reaction.

EXAMPLE 9. PRODUCTION OF INORGANIC SUPPORTED PERACID USING A COLUMN

A 10 g sample of inorganic supported acid produced according to the pre-treatment and stages (i) and (ii) of Example 1 above was placed in a jacketed glass column. A solution consisting of 80 mls methanesulphonic acid to which 20 mls of aqueous 85% w/w hydrogen peroxide solution had been added over 1 hour was circulated through the column for 17 hours at room temperature. Cooling water was then applied to the jacket, and the silica-supported peracid washed with ice/water until the eluent had a pH of 3 to 5. The silica-supported peracid was then vacuum dried as per Example 1.

This gave a supported peracid having an initial avox of 0.44% by weight with 41% of the initial avox remaining after 4 weeks storage at 32° C.

We claim:

1. Organic peracids chemically bonded to an inorganic support, characterised in that they contain a group either of general chemical formula:

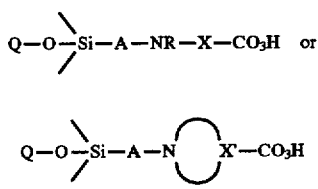 (i)

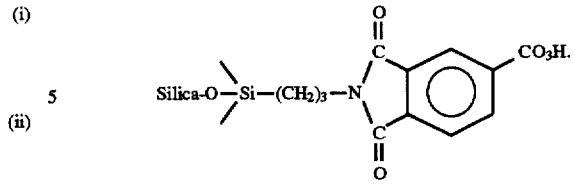

(ii)

where Q represents the inorganic support, A is an aliphatic and/or aromatic bridging group, R represents hydrogen, an alkyl or an aryl group, or a group having the formula X—CO₃H, X represents an alkylene or arylene group and X' represents an alkylene or arylene group.

2. The organic peracid according to claim 1, wherein A comprises a linear alkylene group having from 1 to 10 carbon atoms.

3. The organic peracid according to claim 2, wherein A comprises a linear alkylene group having from 2 to 5 carbon atoms.

4. An organic peracid according to claim 1, wherein X comprises a linear alkylene group having up to 18 carbon atoms.

5. The organic peracid according to claim 4, wherein X comprises a linear alkylene group having from 10 to 14 carbon atoms.

6. An organic peracid according to claims 1, 2, 3, 4 or 5, wherein N—X comprises an amino alkylene or amino arylene group and

comprises a cyclic imido arylene group.

7. An organic peracid according to claim 6, wherein

comprises a phthalimido group.

8. The organic peracid according to claim 1, wherein Q comprises an aluminum, silicon or aluminosilicate based inorganic support.

9. The organic peracid according to claim 1, wherein Q comprises silica gel or a natural or synthetic clay.

10. The organic peracid according to claims 1, 2, 3, 4, 5, 8 or 9, wherein the inorganic support has a surface area in the range of from about 50 m²/g to about 1000 m²/g.

11. The organic peracid according to claim 10, wherein the inorganic support has a surface area in the range of from about 200 m²/g to about 800 m²/g.

12. The organic peracid according to claim 1, 8, or 9, wherein the inorganic support comprises silica gel having a surface area in the range of 250 to 350 m²/g, A is a linear (CH₂)₃ group and N is bonded to two carbonyl groups fused with a benzene ring to form a phthalimido group, the peracid group being bonded directly to the benzene ring in the meta position relative to one carbonyl group and in the para position relative to the other carbonyl to produce an inorganic-supported peracid having the formula:

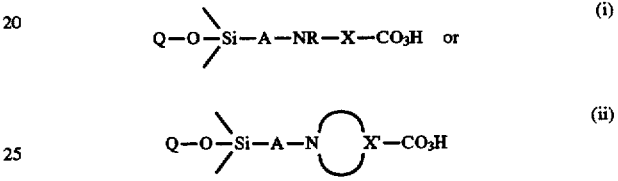

13. The organic peracid according to claim 1 wherein X or X' is oxo-substituted at the alpha position relative to the N.

14. The organic peracid according to claim 1 wherein X or X' separate the peracid group CO₃H from N by from 2 to 6 carbon atoms.

15. A process of producing organic peracids chemically bonded to an inorganic support, characterised in that they contain a group either of general chemical formula:

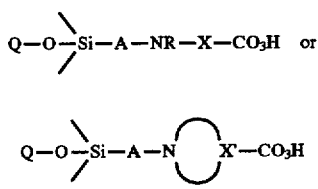 (i)

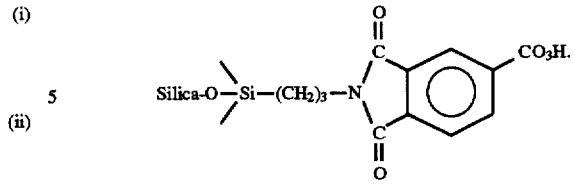

(ii)

where Q represents the inorganic support, A is an aliphatic and/or aromatic bridging group, R represents hydrogen, an alkyl or an aryl group, or a group having the formula X—CO₃H, X represents an alkylene or arylene group and X' represents an alkylene or arylene group comprising the following stages:

Stage (i) Reacting an inorganic support having at least one pendant hydroxy group of formula Q—OH with a silane having the general chemical formula R'₃Si—A—NHY, where A is as defined above, R' represents an alkoxy group and Y represents hydrogen, alkyl or aryl groups, or a group having the formula X—CO₃H to form an intermediate of formula Q—O—Si—A—NHY Stage (ii) Reacting the intermediate from Stage (i) with a compound of formula Z—X—D or ZZ'—X'—D where X and X' are as defined above, Z and Z' represent an oxy- or halogen-containing leaving group and D represents a carboxylic acid group or a functionality capable of conversion thereto to form an intermediate of formula

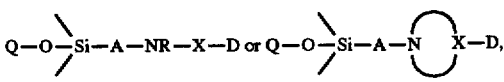

and

Stage (iii) Reacting the intermediate from Stage (ii) with hydrogen peroxide in the presence of a strong acid selected from the group consisting of sulphuric acid, a sulphonic acid, and phosphoric acid thereby producing an inorganic-supported peracid having one of the general formulae described above.

16. The process according to claim 15, wherein stage (i) is carried out in a solvent which is selected from the group consisting of toluene, hydrocarbons, halocarbons and ethers.

17. The process according to claim 15, wherein stage (ii) is carried out in acetic acid solvent.

18. The process according to claim 18, wherein in stage (iii), the strong acid is selected from the group comprising sulphuric acid, methanesulphonic acid, phosphoric acid and mixtures thereof.

19. The process according to claim 15, wherein stage (iii) is carried out at a temperature of up to about 40° C.

20. The process according to claim 15, wherein A comprises a linear alkylene group having from 1 to 10 carbon atoms.

21. The process according to claim 15, wherein A comprises a linear alkylene group having from 2 to 5 carbon atoms.

22. A process according to claim 15, wherein X comprises a linear alkylene group having up to 18 carbon atoms.

23. A process according to claim 22, wherein X comprises a linear alkylene group having from 10 to 14 carbon atoms.

24. A process according to claim 15, wherein N—X comprises an amino alkylene or amino arylene group and N X' comprises a cyclic imido arylene group.

25. A process according to claim 24, wherein

comprises a phthalimido group.

26. A process according to claim 15, wherein Q comprises an aluminum, silicon or aluminosilicate based inorganic support.

27. A process according to claim 15, wherein Q comprises silica gel or a natural or synthetic clay.

28. A process according to claim 15, wherein the inorganic support has a surface area in the range of from about 50 m²/g to about 1000 m²/g.

29. A process according to claim 15, wherein the inorganic support has a surface area in the range of from about 200 m²/g to about 800 m²/g.

30. A process according to claim 15, wherein the inorganic support comprises silica gel having a surface area in the range of 250 to 350 m²/g, A is a linear $(CH_2)_3$ group and N is bonded to two carbonyl groups fused with a benzene ring to form a phthalimido group, the peracid group being bonded directly to the benzene ring in the meta position relative to one carbonyl group and in the para position relative to the other carbonyl to produce an inorganic-supported peracid having the formula:

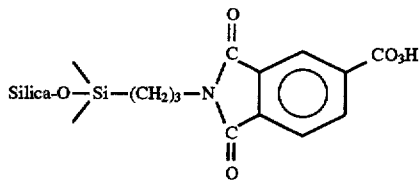

31. A process according to claim 15 wherein X or X' is oxo-substituted at the alpha position relative to the N.

32. The process according to claim 15 or 26 wherein X or X' separate the peracid group $CO_3H$ from N by from 2 to 6 carbon atoms.

* * * * *